United States Patent

Weyer et al.

Patent Number: 5,371,242
Date of Patent: Dec. 6, 1994

[54] PREPARATION OF PRODUCTS OF THE REDUCTION OF 4-HYDROXYBUTYRIC ACID DERIVATIVES

[75] Inventors: Hans-Juergen Weyer, Mannheim; Rolf Fischer, Heidelberg; Werner Schnurr, Herxheim; Norbert Goetz, Worms; Thomas Kuekenhoehner, Boehl-Iggelheim, all of Germany

[73] Assignee: BASF Aktiengesellschaft, Ludwigshafen, Germany

[21] Appl. No.: 110,217

[22] Filed: Aug. 23, 1993

[30] Foreign Application Priority Data

Aug. 29, 1992 [DE] Germany ............... 4228884

[51] Int. Cl.$^5$ ........................... C07D 307/94
[52] U.S. Cl. ........................ 549/331; 549/429; 549/508; 568/852; 568/853
[58] Field of Search ............ 549/330, 429, 508, 331; 568/852, 853

[56] References Cited

U.S. PATENT DOCUMENTS

| | | | |
|---|---|---|---|
| 3,947,503 | 3/1976 | Kummer | 260/635 |
| 3,956,318 | 5/1976 | Suzuki | 549/509 |
| 4,301,077 | 11/1981 | Pesa et al. | 260/346.11 |
| 4,837,346 | 6/1989 | Becker | 549/425 |

FOREIGN PATENT DOCUMENTS

| | | |
|---|---|---|
| 343985 | 11/1989 | European Pat. Off. |
| 284969 | 11/1990 | European Pat. Off. |
| 431923 | 6/1991 | European Pat. Off. |

OTHER PUBLICATIONS

Database WPI, Week 7414, AN 74–25928 (English abstract of JP-B 49 009 464). Mar. 1974.
*Bull. of Chem. Soc. of Japan*, vol. 44, No. 9, Sep. 1971, pp. 2473–2479.
Database WPI, Week 7541, AN 75-68078 (English abstract of JP-A 50 084 505).
*Angewandte Chemie. Intl. Ed.*, vol. 23, No. 12, 1984, pp. 980–981, Huhtasaari et al.
*REDUKTION*, vol. 4/1c, Houben-Weyl, 1980, pp. 404–410.
Japanese Abstract 84/505.
Japanese Abstract 50/1038.
Japanese Abstract 49/9463.

*Primary Examiner*—C. Warren Ivy
*Assistant Examiner*—A. A. Owens
*Attorney, Agent, or Firm*—Keil & Weinkauf

[57] ABSTRACT

Abstract of the Disclosure: Products of the reduction of 4-hydroxybutyric acid derivatives of the formula IIa

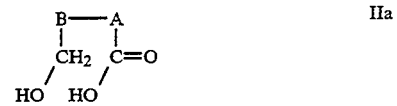

where one of A and B is methylene and the other is cyclopropylidene, or of $C_1$—$C_4$—alkyl esters (IIb) or lactones (IIc) of these acids IIa, are prepared by hydrogenating the compounds IIa or IIb or IIc catalytically using hydrogen in the presence of a heterogeneous hydrogenation catalyst, giving novel compounds which can be used to prepare polymers.

5 Claims, No Drawings

PREPARATION OF PRODUCTS OF THE REDUCTION OF 4-HYDROXYBUTYRIC ACID DERIVATIVES

The present invention relates to a process for the preparation of products (I) of the reduction of 4-hydroxybutyric acid derivatives of the formula IIa

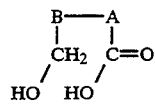
IIa where one of A and B is methylene and the other is cyclopropylidene, or of C₁-C₄—alkyl esters (IIb) or lactones (IIc) of these acids (IIa). The invention furthermore relates to novel products of the reaction of II, and to polymers which can be prepared from these novel compounds.

In detail, the reaction products I are the following compounds:

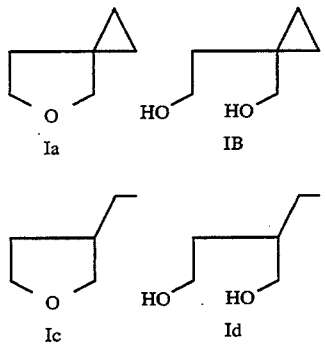

As is known, 2-substituted butanediols are important as components of polyesters, while 3-substituted tetrahydrofurans are used as comonomers for copolymerization with tetrahydrofuran. Thus, 3-methyltetrahydrofuran is used for the preparation of polymers from which elastic fibers can be produced (EP-A-343 985). Compounds containing substituents other than methyl have hitherto been difficult to obtain or, in the case of the compounds Ia and Ib, were unknown.

3-Hydroxymethylpentanol Id can be obtained by hydrogenating 4-ethyl-3,6-dihydro-1,2-dioxin according to JP-A 50/84,505.

3-Ethyltetrahydrofuran Ic can be prepared by catalytic hydrogenation of 3-ethyl-3,4-epoxybutanol according to U.S. Pat. Nos. 3,956,318. JP-A 49/9463, JP-A 49/9464 and JP-A 50/1038 relate to the preparation of 3-alkyltetrahydrofuran from alkylmaleic acids. A common feature of all the starting compounds is that they can only be prepared by complex methods.

It is an object of the present invention to provide a process which gives novel substituted tetrahydrofurans or the corresponding diols and is furthermore capable of making 3-ethyltetrahydrofuran, which is known per se, more readily accessible.

We have found that this object is achieved by a process for the preparation of the compounds I from the compounds II, which comprises hydrogenating the compounds IIa or IIb or IIc using hydrogen in the presence of a heterogeneous hydrogenation catalyst.

The present invention also provides the novel compounds Ia and Ib and polymers built up from Ia.

The starting compounds IIa and IIb are obtainable by methods known per se from the compounds IIc

Preference is given to compounds where A is cyclopropylidene and B is methylene.

Thus, 5-oxa[2,4]spiroheptan-6-one is disclosed in Bull. Chem. Soc. Jap. 44 (1971) 2473. However, preference is given to 5-oxa[2,4]spiroheptan-4-one (IIc′)

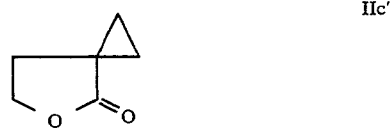

IIc′ is obtained in relatively large amounts in the preparation of methyl tetrahydropyran-4-carboxylate, as described in EP-A 284 969. The compound named in Example 1 therein as 3-vinylbutyrolactone is in fact IIc′.

The starting compounds II are reacted on hydrogenation catalysts. These are generally conventional catalysts, as described, for example, in Houben-Weyl, Methoden der organischen Chemie, Vol. 4/1c, pp. 15 to 28, Thieme Verlag, 1980. Preferred hydrogenation catalysts are those which contain copper and/or metals from groups 8 to 10 of the IUPAC Periodic Table, particular preference being given to cobalt, nickel, ruthenium, rhodium, palladium and platinum. The catalysts can be used with or without a carrier; the type of carrier is generally not crucial. Conventional carrier materials, such as silicon dioxide, aluminum oxide, titanium oxide, activated charcoal, silicates and zeolites, are therefore suitable.

The supported catalysts can be prepared in the presence of binders or molding aids. Such catalysts can be employed in the form of grit, extrudates or beads.

Weight hourly space velocities of from 0.01 to 1 kg, in particular from 0.05 to 0.3 kg of II per liter of catalyst and per hour have proven successful.

The hydrogenation can be carried out in the presence of a solvent. Suitable solvents are polar solvents such as ethers, alcohols or water, or mixtures of these. Preference is given to ethers and alcohols having up to six carbon atoms, such as ethanol, n-propanol, isopropanol and n-butanol.

The temperature during the hydrogenation can be from 50° to 400° C., in particular from 150° to 300° C. The pressure can be selected within broad limits, extending from 1 to 400 bar, in particular from 50 to 300 bar. The process can be carried out continuously or batchwise. Examples of suitable reactors are tubular reactors and tube-bundle reactors.

The process according to the invention can advantageously be utilized for the preparation of predominant amounts of Ib or Ic.

Thus, the proportion of Ic in the reaction product can be greatly increased if IIc′ is hydrogenated at from 200° to 400° C. and in the presence of acidic compounds. The latter include protonic acids, such as sulfuric acid, hydrochloric acid and phosphoric acid, Lewis acids, such as boron trifluoride and zinc chloride, and furthermore zeolites, cation exchangers, silicates, aluminum oxides, aluminum phosphates and other acidic metal oxides. These compounds can be added to the reaction mixture. However, it is advantageous to use the acidic compounds with the catalyst in the form of the catalytically active components applied to an acidic carrier.

The proportion of compound I$b$ in the reaction product can be greatly increased if II$c'$ is hydrogenated at from 50° to 200° C. on neutral catalysts.

The reaction products I are isolated by known methods, preferably by distillation.

Compound I$a$ can be converted into polymers by cationic polymerization. Copolymerizable monomers which may be mentioned in particular are tetrahydrofuran and 3-methyltetrahydrofuran.

The process according to the invention allows the preparation of a novel 3-substituted tetrahydrofuran and of the corresponding diol, and the synthesis of 3-ethyltetrahydrofuran in good yield.

EXAMPLES

Catalyst composition

All percentages are by weight.

Catalyst A 67% of CoO, 19.8% of CuO, 7% of Mn$_2$O$_3$, 3% of MoO$_3$, 0.2% of Na$_2$O and 3% of H$_3$PO$_4$ (as in EP-B 100 406; p. 2, line 63, to p. 3, line 11)

Catalyst B 50% of NiO, 17% of CuO, 31% of γ-Al$_2$O$_3$ and 2% of MoO$_3$ (as in EP-A 18 569, p. 2, line 27, to p. 3, line 18)

Catalyst C 36.5% of CuO, 1.0% of BaO, 0.6% of Cr$_2$O$_3$, 0.4% of ZnO, 14.4% of MgO, 28.5% of SiO$_2$ and 18.6% of H$_2$O (as in DE-A 869 052, p. 1 to p.2, line 15)

Catalyst D 40% of CuO, 40% of ZnO, 20% of γ-Al$_2$O$_3$ and 0.1% of Na$_2$O (as in DE-A 1 542 632, p. 2 to p. 4, line 2)

Catalyst E 56% of CuO and 44% of γ-Al$_2$O$_3$ (as in EP-A 44 444, p. 8, line 33, to p. 11, line 1)

EXAMPLES 1 TO 9

10 g of II$c'$ were hydrogenated as a batch in 100 ml of n-butanol in the presence of 20 ml of catalyst (2.5 to 4 nun grit) at a hydrogen pressure of 200 bar and at various temperatures T. When the reaction was complete, the reaction products were analyzed by gas chromatography.

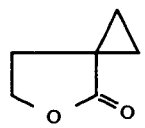

II$c'$

| Ex. | Catalyst | T [°C.] | Yield* | | | |
|---|---|---|---|---|---|---|
| | | | Ia | Ib | Ic | Id |
| 1 | A | 150 | 0 | 84 | 2 | 14 |
| 2 | B | 175 | 5 | 23 | 71 | 1 |
| 3 | C | 150 | 0 | 93 | 0 | 7 |
| 4 | D | 175 | 1 | 87 | 1 | 11 |
| 5 | D | 200 | 2 | 55 | 11 | 32 |
| 6 | D | 225 | 1 | 0 | 94 | 6 |
| 7 | E | 150 | 1 | 88 | 2 | 9 |
| 8 | E | 175 | 22 | 46 | 23 | 3 |

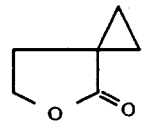

II$c'$

| Ex. | Catalyst | T [°C.] | Yield* | | | |
|---|---|---|---|---|---|---|
| | | | Ia | Ib | Ic | Id |
| 9 | E | 200 | 27 | 0 | 73 | 0 |

*The reactor product contains, in addition to compounds Ia to Id, small amounts of unidentified compounds.

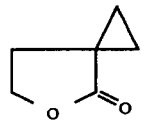

Ia

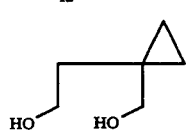

Ib

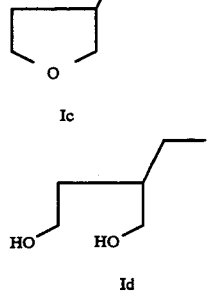

Ic

Id

EXAMPLE 10

3.6 g of II$c'$ in 14 ml of methanol were reacted per hour by the trickle procedure on 18 g of catalyst C in the form of 2.5 to 4 mm grit in a fixed bed at 200° C., a hydrogen pressure of 200 bar and a weight hourly space velocity of 0.12 kg of II$c'$/liter of catalyst and per hour. The yield of Ib was 45%, and that of Ic was 35%. The conversion of II$c'$ was quantitative.

5-Oxa-[2,4]-spiroheptane:
b.p. 112° C./1013 mbar
$^1$H-NMR (CDCl$_3$): 3.97 (2H, t, J=7 Hz), 3.64 (2H, s); 1.88 (2H, t, J=7 Hz); 0.68–0.65 (2H, m), 0.62–0.59 ppm (2 H, m).
$^{13}$C-NMR (CDCl$_3$): 75.0 (CH$_2$); 68.7 (CH$_2$); 35.4 (CH$_2$); 22.4 (C); 10.8 ppm (2×CH$_2$).

2-(1-Hydroxymethylcyclopropyl)ethanol I$b$:
b.p. 113° C./1 mbar
1H-NMR (CDCl$_3$): 4.77 (2H, s, OH); 3.68 (2H, t, J=5 Hz); 3.38 (2H, s); 1.60 (2H, t, J=5 Hz); 0.48 (2H, dd, J$_1$=6 Hz, J$_2$=4 Hz); 0.38 ppm (2H, dd, J$_1$=6 Hz, J$_2$=4 Hz). $^{13}$C-NMR (CDCl$_3$): 69.9 (CH$_2$); 61.1 (CH$_2$); 39.8 (CH$_2$); 21.7 (C); 10.9 ppm (2×CH$_2$).

We claim:

1. A process for the preparation of products (I) of he reduction of 4-hydroxybutyric acid derivatives of the formula II$a$

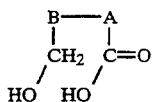

where one of A and B is methylene and the other is cyclopropylidene, or of $C_1$-$C_4$—alkyl esters (IIb) or lactones (IIc) of these acids IIa, which comprises hydrogenating the compounds IIa or IIb or IIc catalytically using hydrogen in the presence of a heterogeneous hydrogenation catalyst at a temperature of from 50° to 400° C. and at a pressure of from 1 to 400 bar.

2. A process as defined in claim 1, wherein a compound IIc is used where A is cyclopropylidene and B is methylene.

3. A process as defined in claim 1, wherein a catalyst is used which contains copper and/or metals from groups 8 to 10 of the Periodic Table.

4. 5-Oxa [2,4 ]spiroheptane

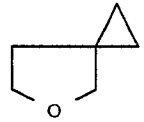

5. 2- (1-Hydroxymethylcyclopropyl )ethanol

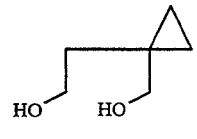

* * * * *